United States Patent [19]

Mulhollan

[11] Patent Number: 5,234,455
[45] Date of Patent: Aug. 10, 1993

[54] LIPPED CANNULA AND METHODS OF INTRODUCING SURGICAL INSTRUMENTS IN ARTHROSCOPIC SURGICAL PROCEDURES

[75] Inventor: James S. Mulhollan, Little Rock, Ark.

[73] Assignee: Arkansas Knee Clinic, P.A., Little Rock, Ark.

[21] Appl. No.: 839,150

[22] Filed: Feb. 20, 1992

[51] Int. Cl.$^5$ ............................................. A61M 25/00
[52] U.S. Cl. ..................................... 606/191; 604/164
[58] Field of Search ................ 606/191, 185; 604/264, 604/164, 165, 174

[56] References Cited

U.S. PATENT DOCUMENTS

| | | | |
|---|---|---|---|
| 2,899,960 | 8/1959 | Ginsburg . | |
| 3,783,454 | 1/1974 | Sausse et al. . | |
| 3,896,804 | 7/1975 | Ekbladh et al. . | |
| 3,952,742 | 4/1976 | Taylor | 604/164 |
| 3,958,557 | 5/1976 | Sharp et al. . | |
| 4,077,412 | 3/1978 | Moosson | 604/174 |
| 4,642,101 | 2/1987 | Krolikowski et al. | 604/164 |
| 5,002,557 | 3/1991 | Hasson | 606/191 |
| 5,009,643 | 4/1991 | Reich et al. | 604/165 |
| 5,122,122 | 6/1992 | Allgood | 604/174 |
| 5,147,316 | 9/1992 | Castillenti | 604/164 |

Primary Examiner—Stephen C. Pellegrino
Assistant Examiner—William Lewis

[57] ABSTRACT

A lipped cannula includes a cylindrical member having a distal end for being inserted through a portal of minimal size in anatomical tissue of a wall of the body, a proximal end and a lip spaced proximally from the distal end and a housing mounting the proximal end of the cylindrical member. The lip has a periphery that is spaced outwardly from the circumference of the cylindrical member allowing a surface of the lip to engage an internal surface of the anatomical tissue when the distal end of the cannula is inserted in the body to prevent the distal end from backing out of the body. A lumen of the lipped cannula allows various surgical instruments to be inserted at an operative site in the body through the lumen with the lipped cannula preventing extravasation. A method of introducing a surgical instrument at an operative site in the body in endoscopic procedures includes the steps of forming a portal of minimal size in tissue of a wall of the body adjacent the operative site, inserting an end of a cannula into the body through the portal, positioning a lip of the cannula within the body against an internal surface of the wall to prevent backing out of the cannula from the body and introducing a surgical instrument at the operative site through a lumen of the cannula.

25 Claims, 1 Drawing Sheet

LIPPED CANNULA AND METHODS OF INTRODUCING SURGICAL INSTRUMENTS IN ARTHROSCOPIC SURGICAL PROCEDURES

BACKGROUND OF THE INVENTION

1. Field of the Invention

The present invention pertains to cannulas having lumens for receiving surgical instruments and, more particularly, to cannulas for being inserted in the body through portals of minimal size allowing various surgical instruments to be introduced in the body via the lumens of the cannulas.

2. Description of the Prior Art

Various least invasive medical procedures involve introducing instruments at operative sites in the body through portals of minimal size formed, such as by puncture or stab wounds, in anatomic walls of the body allowing diverse procedures to be conducted at the operative sites with the operative sites being viewed endoscopically. Such walls include the external skin and underlying soft tissue as well as tissue forming walls of cavities in the body as well as other anatomical structure required to be penetrated to access operative sites in the body. Least invasive medical procedures are particularly useful in joints or articulations of the body, i.e., the connections of the various surfaces of the bones of the body and, especially, the knee, allowing various surgical procedures, such as cartilage repair and ligament repair and reconstruction, to be performed through minimal size portals with the knee being visualized with an arthroscope. Least invasive, closed or endoscopic, surgical procedures possess many advantages over open surgical procedures wherein relatively long incisions are utilized to access an operative site in the body including minimal invasiveness and trauma, reduced hospitalization and rehabilitation times, performance of surgery on an out-patient basis, decreased patient discomfort, enhanced post-surgical mobility and cosmetically pleasing wounds. Accordingly, it is preferred to perform many surgical procedures least invasively, or endoscopically, utilizing very small or narrow portals to access operative sites in the body. In many least invasive surgical procedures, such as arthroscopic posterior cruciate ligament repair and reconstruction of the knee wherein posterolateral or posteromedial portals are formed through the external skin and underlying soft tissue adjacent the knee, the thickness of the tissue forming the walls of the body that must be penetrated to access the operative sites can be considerable such that it is not feasible to introduce and remove instruments directly through portals formed in the tissue of the walls. Accordingly, cannulas are usually inserted through the portals allowing various sizes and types of instruments to be introduced at and removed from the operative sites via lumens of the cannulas with the lumens of the cannulas providing a smooth passage enhancing insertion and removal of the instruments. When inserting cannulas through portals formed in walls of the body, it is desirable that ends of the cannulas disposed within the body remain as close as possible to internal surfaces of the walls such that the ends of the cannulas do not protrude very far into the body to avoid inadvertent contact with and damage to anatomical structure, such as organs, nerves, muscles and other delicate anatomic structure within the body. However, a problem exists with cannulas for receiving medical instruments in that, once the cannulas are inserted through anatomic walls, the cannulas can easily back out of the walls thusly comprising the surgical procedure. Accordingly, there is a need in least invasive, or endoscope, surgical procedures and, in particular, in arthroscopic posterior cruciate ligament procedures of the knee, for cannulas that avoid backing out of anatomic walls through which they are inserted while permitting ends of the cannulas disposed within the body to remain very close to internal surfaces of the walls. Another problem associated with introducing surgical instruments at operative sites in the body through portals formed in tissue of walls of the body is that extravasation can occur; and, therefore, the need exists to prevent extravasation when introducing surgical instruments through portals formed in anatomical walls.

Tubular conduits, such as catheters and needles, for being introduced into the body and having structure, such as rings and collars, for anchoring the conduits in the body have been proposed, and U.S. Pat. No. 4,642,101 to Krolikowski et al, U.S. Pat. No. 3,896,803 to Ekbladh et al, U.S. Pat. No. 3,783,454 to Sausse et al and U.S. Pat. No.2,899,960 to Ginsburg are illustrative of such devices. A disadvantage of such devices is that the conduits are limited to fluid transmission with the body and do not allow instruments to be introduced in the body through the conduits.

SUMMARY OF THE INVENTION

Accordingly, it is a primary object of the present invention to overcome the above-mentioned disadvantages of prior art cannulas for introducing surgical instruments at operative sites in the body and methods of introducing surgical instruments in the body via cannulas in endoscopic procedures.

Another object of the present invention is to provide a cannula for accessing an operative site in the body through a portal of minimal size formed in tissue of a wall of the body, the cannula having a lumen for introducing surgical instruments at the operative site and a lip at an end of the cannula to be disposed in the body for preventing backing out of the cannula from the wall.

A further object of the present invention is to prevent extravasation when inserting surgical instruments at operative sites in the body through portals of minimal size formed in tissue of walls of the body.

An additional object of the present invention is to provide a cannula for introducing surgical instruments at operative sites in the body via a lumen of the cannula with the cannula inserted in the body through a portal formed in tissue of a wall of the body, the cannula having a lip to be disposed against an internal surface of the wall to prevent inadvertent removal of the cannula from the wall.

It is also an object of the present invention to provide a cannula for accessing an operative site in the body through a portal formed in tissue of a wall of the body and having a lip on an end of the cannula to be disposed in the body for engaging an internal surface of the wall to prevent backing out of the cannula from the wall with the end protruding only a short distance into the body.

A further object of the present invention is to provide a cannula for being inserted in the body through a portal formed in tissue of a wall of the body and having a lumen for receiving various sizes of instruments and a lip on an end of the cannula to be disposed in the body for engaging an internal surface of the wall preventing unintentional withdrawal of the cannula from the body when introducing and withdrawing instruments through the lumen.

Yet another object of the present invention is to provide a method of introducing surgical instruments at an operative site in the body in endoscopic procedures including inserting a cannula in the body through a portal of minimal size in tissue forming a wall of the body, engaging an internal surface of the wall with a lip of the cannula disposed in the body and inserting a surgical instrument at the operative site through the cannula from externally of the body.

An additional object of the present invention is to provide a method of preventing extravasation when introducing surgical instruments at an operative site in the body in endoscopic procedures including inserting a cannula in the body through a portal of minimal size in tissue of a wall of the body, engaging an internal surface of the wall with a lip of the cannula disposed in the body and inserting a surgical instrument at the operative site through the cannula with ends of the cannula and the instrument being disposed externally of the body.

Another object of the present invention is to provide a method of introducing surgical instruments at the knee in arthroscopic procedures including inserting a cannula via a posteromedial or posterolateral portal in tissue adjacent the knee, engaging the tissue with a lip of the cannula and introducing surgical instruments at the knee through the cannula.

Some of the advantages of the present invention are that insertion of surgical instruments through walls of the body having relatively great thicknesses is facilitated, instruments of various sizes can be inserted through the lumen of the cannula with the cannula being inserted through a portal just large enough to receive the cannula, inadvertent contact with and damage to structure, such as muscles, tendons, organs and nerves, within the body is avoided, endoscopic procedures are facilitated, arthroscopy of the knee and, in particular, arthroscopic posterior ligament repair and reconstruction of the knee, is enhanced and arthroscopic posterior cruciate repair and reconstruction as well as meniscus repair of the knee can be accomplished via posteromedial and posterolateral portals.

Accordingly, these and other objects and advantages are obtained with the present invention as characterized in a lipped cannula including a cylindrical member having a distal end for being inserted through a portal of minimal size in anatomical tissue forming a wall of the body, a proximal end and a housing mounting the proximal end of the cylindrical member. A lip on the cylindrical member spaced proximally from the distal end has a periphery that is spaced outwardly from the circumference of the cylindrical member such that a surface of the lip engages an internal surface of the anatomical tissue with the distal end of the cannula inserted in the body to prevent the distal end of the cannula from backing out of the body. The lip is disposed proximally of the distal end a minimal distance such that, with the surface of the lip against the internal surface of the tissue, the cannula protrudes into the body only a short distance from the internal surface to avoid contact with and possible damage to anatomic structure within the body. The lip is formed by a protrusion having a truncated conical configuration facilitating insertion through the tissue of the wall. Various surgical instruments can be inserted at an operative site in the body via a lumen of the cannula with the cannula preventing extravasation when introducing instruments at operative sites in the body from endoscopic size portals. Methods of introducing surgical instruments at operative sites in the body in endoscopic procedures and, in particular, arthroscopic procedures of the knee, include the steps of forming a portal of minimal size in tissue of a wall of the body adjacent the operative site, inserting an end of a cannula into the body through the portal, positioning a lip of the cannula within the body against an internal surface of the wall to prevent backing out of the cannula from the body and introducing surgical instruments at the operative site through a lumen of the cannula.

Other objects and advantages of the present invention will become apparent from the following description of the preferred embodiments taken in conjunction with the accompanying drawings wherein like parts in each of the several figures are identified by the same reference characters.

DESCRIPTION OF THE PREFERRED EMBODIMENTS

Figure 1:
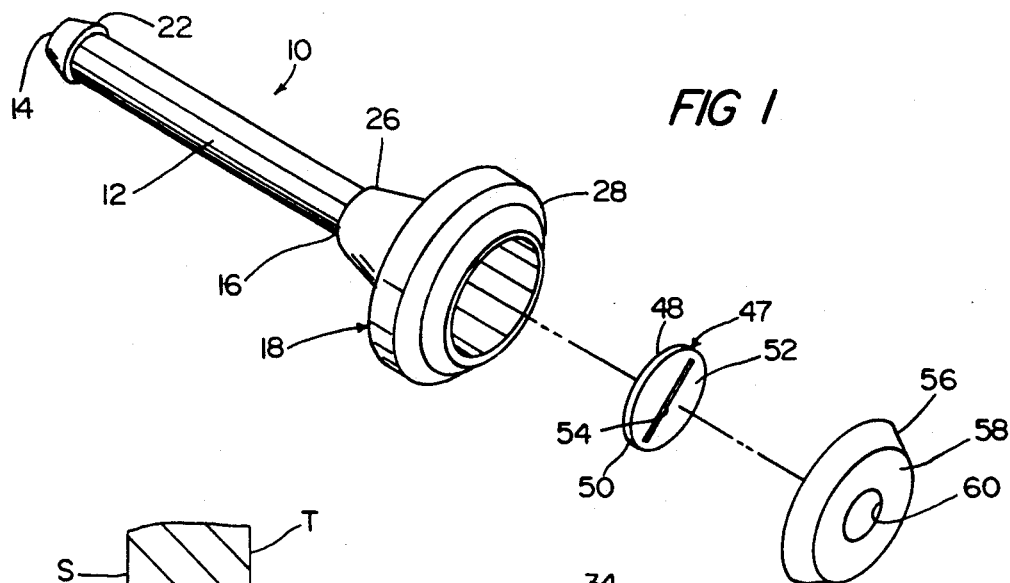
FIG. 1 is a perspective view of a lipped cannula according to the present invention.
Figure 2:
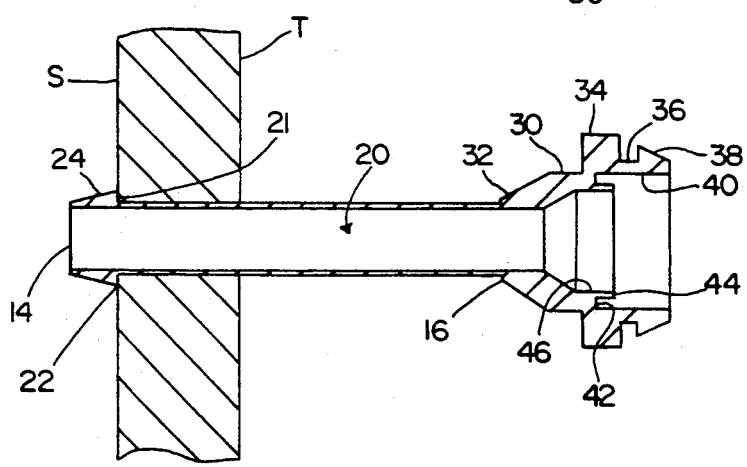
FIG. 2 is a sectional view of the lipped cannula of FIG. 1 showing the lipped cannula inserted through a portal in anatomic tissue forming a wall of the body.

A lipped cannula according to the present invention is shown at 10 in FIGS. 1 and 2 and includes an elongate, cylindrical member 12 having a distal end 14 and a proximal end 16 joined to a housing 18 mounting the proximal end 16 of the cylindrical member 12. The cylindrical member 12 is preferably made from stainless steel and has a lumen 20 disposed longitudinally therein extending from distal end 14 to proximal end 16. The lumen 20 preferably has a circular configuration in cross-section and a diameter sized to receive various sizes of surgical instruments to be introduced at an operative site in the body. The cylindrical member 12 is preferably tubular in external configuration and has an outer diameter to be received in portals of very small size formed in anatomical tissue of a wall of the body. An annular lip 22 is formed on the cylindrical member 20 by a protrusion 24 having a truncated conical configuration such that the protrusion 24 tapers in a distal direction from the lip 22 to the distal end 14 with the annular lip 22 being disposed proximally of the distal end 14 a short distance. The lip 22 has an outer diameter or periphery disposed concentrically with the cylindrical member 20, such that the outer diameter or periphery of the cross-sectional configuration of the cylindrical member is within the periphery of the lip and, preferably, the peripheries are concentric. The outer diameter or periphery of the lip is rigidly or immovably disposed outwardly from the cross-sectional periphery or circumference of the cylindrical member allowing a planar or flat or substantially planar or flat surface 21 of the lip extending from the periphery or circumference of the cylindrical member to the outer diameter or periphery of the lip to engage an internal surface of a wall of the body with the tapered configuration of the protrusion 24 facilitating insertion of the distal end 14 through tissue forming the wall. Although the protrusion 24 is shown as being truncated conical in configuration, it will be appreciated that the protrusion can have various other tapered configurations facilitating insertion through a wall of the body and, where the thickness of the wall is minimal presenting little resistance to insertion of the lipped cannula, the protrusion can have various non-tapered configurations. The lip 24 can have various configurations in addition to the annular configuration shown to provide a peripheral edge that is rigidly or immovably spaced outwardly from the circumference or periphery of the cylindrical member 12 so as to define a surface substantially perpendicular to a longitudinal axis of the cylindrical member for engaging an internal surface of the wall of the body. The cylindrical member 12 can have various tubular and non-tubular configurations having a circumference or periphery in cross-section disposed inwardly of the lip 22. It will be appreciated that the cylindrical member 12 can be formed as a single piece of unitary, integral construction or as multiple pieces joined by techniques such as welding, and that the protrusion 24 can be formed integrally, unitarily with the cylindrical member 12 or separately therefrom.

The housing 18 is preferably made of stainless steel and includes a forward section 26 joined to the proximal end 16 of the cylindrical member 12 and a rearward section 28 joined to the forward section 26. The forward section 26 includes a cylindrical segment 30 and a tapered segment 32 joined distally to the cylindrical segment 30 with the tapered segment 32 tapering in a distal direction from the cylindrical segment 30 to a forward end of the housing 18, the proximal end 16 of the cylindrical member 12 being joined to the tapered segment 32 at the forward end. The rearward section 28 includes an annular, peripheral flange 34 joined externally to the cylindrical segment 30 and having an outer diameter greater than the outer diameter of the cylindrical segment to facilitate grasping of the housing 18 during use. A cylindrical projection 36 extends from the flange 34 in a proximal direction, the projection 36 terminating proximally at a tapered rim 38. The rim 38 tapers in a proximal direction from a surface joined to the projection 36 to a rearward end of the housing 18, and an internal, cylindrical passage 40 is formed in the rearward section 28 of the housing. The passage 40 preferably has a circular configuration in cross-section with the cross-section of the passage 40 being substantially constant along the length of the passage 40. The passage 40 extends longitudinally from the rearward wall in a distal direction to an internal shoulder 42 in the rearward section 28. An annular ledge 44 extends proximally, longitudinally from the shoulder 42 a short distance, the ledge 44 being disposed within the passage 40 concentrically with an internal wall of the rearward section 28. The ledge 44 surrounds an opening to an internal cavity 46 of the housing 18, the cavity 46 communicating with the passage 40 at the opening and having a cylindrical segment in the rearward section 28, a distally tapered segment within the forward section 26 and a cylindrical segment joining the tapered segment to the lumen of the cylindrical member. The passage 40 and the cavity 46 are longitudinally and, preferably, coaxially, aligned providing a continuous, longitudinal channel or lumen through the cylindrical member 12 and the housing 18. A valve assembly 47, such as a slit-type valve 48, can be mounted in the passage 40 with an annular wall 50 of the valve disposed around the ledge 44 and a face 52 of the valve extending across the opening of the cavity 46 allowing instruments to be inserted through a slit 54 in the face 52 of the valve. A cap or seal 56 can be placed over the rim 38 of the housing 18 such that a face 58 of the cap extends across an opening to passage 40 at the rearward end of the housing, and a circular aperture 60 is provided in the face 58 of the cap to allow surgical instruments to be inserted through the lipped cannula 10.

It will be appreciated that the housing 18 can have various configurations in addition to those shown herein as illustrative to allow the housing to be grasped and held, externally of the body, when inserting the lipped cannula 10 through portals and when introducing surgical instruments through the cannula. The housing 18 can be formed integrally, unitarily with the cylindrical member 12 or the housing can be formed separately from the cylindrical member with the housing and the cylindrical member joined by techniques such as welding. Various types and configurations of valve assemblies can be provided for use with the housing 18 allowing instruments of various sizes to be inserted through the valve assemblies with the valve assemblies creating a seal around the instruments. Where a slit-type valve 48 is utilized, it is preferred that the valve be made from a resilient material, such as silicone rubber, such that the material of the valve deforms and seals around instruments of various sizes inserted through the slit. The cap 56 can have various configurations and arrangements, and the cap can be formed of a resilient, deformable material such as rubber allowing the material of the face to stretch and seal around instruments of various sizes inserted through the aperture 60. The valve assembly and cap can be removable from the housing 18 permitting other valve assemblies and caps having different sized slits and apertures to be mounted on the housing.

Although the exact configuration and dimensions for the lipped cannula 10 can vary, in a preferred embodiment the overall length of the lipped cannula from the distal end 14 to the rearward wall of the housing 18 is approximately 3.067 inches, the outer diameter of the cylindrical member 12 is approximately 0.360 inches, the outer diameter of the lip 22 is approximately 0.412 inches, the distance from the distal end 14 to the lip 22, i.e., the length of the protrusion 24, is approximately 0.125 inches and the diameter of the lumen 20 is approximately 0.325 inches.

According to a method of operation for the lipped cannula 10 in introducing surgical instruments at operative sites in the body in endoscopic procedures, a portal of minimal size is formed in tissue, such as tissue T shown in FIG. 2, of a wall, such as formed by skin and underlying soft tissue and walls of anatomical body cavities, of the body adjacent an operative site in the body, the portal being formed with a penetrating instrument, such as a trocar. Once the portal has been formed, the lipped cannula 10 is inserted through the portal such that the distal end 14 of the cylindrical member 12 is disposed in the body as shown in FIG. 2 with the housing 18 held externally of the body. During insertion of the lipped cannula 10 through the tissue T, the tapered configuration of the protrusion 24 facilitates insertion of the lipped cannula through the wall of the body and, once inserted, the distal end 14 of the lipped cannula 10 protrudes from an internal surface S of the wall as shown in FIG. 2. The lip 22 is positioned against the internal surface S by moving the cylindrical member 22 via the housing 18 externally of the body and the lip, via engagement of the surface 21 with the internal surface S, prevents the lipped cannula 10 from backing out from the wall, the lip 22 resisting withdrawal of the lipped cannula 10 from the wall. With the lip 22 engaging the internal surface S, the distal end 14 of the lipped cannula 10 protrudes from the internal surface a short distance such that contact with and possible damage to anatomic structure within the body is avoided. A surgical instrument selected in accordance with the surgical procedure to be performed at the operative site is introduced through the lipped cannula 10, the surgical instrument extending through the cap 56, the valve assembly 48 and the lumen of the lipped cannula and exiting the distal end 14 for positioning at the operative site with the operative site being viewed endoscopically. Upon completion of the procedure to be performed by the instrument, the instrument is withdrawn from the operative site through the lumen of the lipped cannula 10, and various other diverse sizes and types of instruments can be introduced at the operative site via the lumen of the lipped cannula. Once the surgical procedure has been completed, the lipped cannula 10 is withdrawn from the body by manually pulling, via the housing 18, the lipped cannula from the wall, and the tissue of the wall can be manipulated or spread to facilitate withdrawal of the lipped cannula. It will be appreciated that the lipped cannula 10 can be inserted in the body after the portal has been formed in the wall with the penetrating instrument or that the lipped cannula 10 can be inserted during formation of the portal by mounting the penetrating instrument in the lumen of the lipped cannula such that the lipped cannula moves through the tissue along with the penetrating instrument allowing the penetrating instrument to be removed from the lipped cannula leaving the lipped cannula in place.

Figure 3:
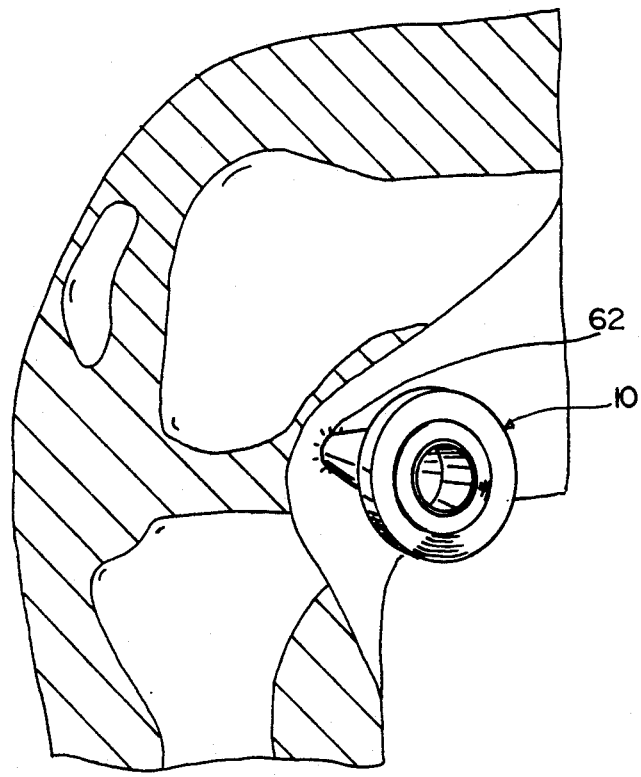
FIG. 3 is a side view of the right knee showing the lipped cannula of FIG. 1 inserted through a posterolateral portal.

The lipped cannula 10 of the present invention is useful in various types of endoscopic procedures to provide access to operative sites in the body via endoscopic size portals allowing surgical instruments to be introduced at the operative sites through the lipped cannula with the lipped cannula being prevented from backing out from the body until the endoscopic procedures have been completed and the lipped cannula is intentionally withdrawn. The lipped cannula 10 is particularly useful in endoscopic procedures wherein the thicknesses of the walls through which the surgical instruments must be inserted are considerable, and the lipped cannula provides a smooth passage for surgical instruments inserted through walls having relatively great thicknesses. The lipped cannula 10 is particularly useful in arthroscopic procedures, such as posterior cruciate ligament repair and reconstruction and meniscus repair, of the knee wherein access to the knee must be made from posteromedial or posterolateral portals formed in tissue adjacent the knee, the skin and underlying tissue posterolaterally and posteromedially being of relatively great thickness. According to a method of operation for the lipped cannula 10 in introducing surgical instruments at the knee in arthroscopic procedures, such as posterior cruciate ligament repair and reconstruction and meniscus repair, a portal, such as posterolateral portal 62 shown in FIG. 3, is formed posterolateral or posteromedial in tissue, including the skin and underlying soft tissue, adjacent the knee with the knee being visualized with an arthroscope. The lipped cannula 10 is inserted through the portal 62 such that the distal end 14 is disposed within the body, and the surface 21 of the lip 22 is positioned against an internal surface of the tissue to prevent backing out of the lipped cannula from the knee. With the lip 22 engaging the internal surface of the tissue, the distal end 14 protrudes from the internal surface only a short distance such that contact with tendons and nerves of the knee is avoided. Surgical instruments selected in accordance with the procedure to be performed are introduced at the knee through the lipped cannula 10, the lipped cannula providing a smooth passage for introducing the surgical instruments at the knee through the relatively thick tissue while preventing extravasation. Upon completion of the surgical procedure and removal of the surgical instruments, the lipped cannula is withdrawn from the tissue of the knee and the portal is closed.

Accordingly, the lipped cannula and methods of introducing surgical instruments at operative sites in the body in endoscopic procedures facilitate various endoscopic procedures and, in particular, arthroscope procedures such as posterior cruciate ligament repair and reconstruction of the knee wherein the knee is accessed from posteromedial or posterolateral portals, prevent extravasation when introducing surgical instruments at operative sites in the body via portals of minimal size, allow the lipped cannula to be anchored relative to a wall of the body while protruding into the body only a short distance, facilitate insertion through tissue of an anatomical wall, provide a smooth passage for introducing surgical instruments through portals in tissue of anatomical walls and, in particular, walls having relatively great thicknesses, allow various sizes and types of surgical instruments to be introduced via the lumen of the lipped cannula with the lipped cannula being inserted through a portal just large enough to accommodate the lipped cannula, avoid inadvertent contact with anatomic structure in the body and prevent withdrawal of the lipped cannula from the body except upon completion of the surgical procedure when the lipped cannula can be intentionally withdrawn.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A cannula for introducing surgical instruments in the body through a portal of minimal size formed in a wall of anatomical tissue including
    an elongate member having a distal end to be inserted through the portal into the body, a proximal end and a cross-sectional configuration having a periphery;
    a housing mounting said proximal end of said cylindrical member to be disposed externally of the body;
    a lumen through said cylindrical member and said housing providing a passage for receiving surgical instruments to be introduced in the body; and
    a lip on said elongate member proximally spaced from said distal end and having a periphery immovably spaced outwardly from said periphery of said elongate member to be disposed within the body, said lip including a substantially planar surface for engaging the wall of the body with said distal end inserted in the body to prevent backing out of said distal end from the body.

2. A cannula as recited in claim 1 wherein said periphery of said elongate member is disposed within said periphery of said lip.

3. A cannula as recited in claim 2 wherein said lip is defined by a protrusion on the elongate member, said protrusion tapering in a distal direction from said surface to said distal end.

4. A cannula for introducing surgical instruments in the body through a portal of minimal size formed in a wall of anatomical tissue including
- an elongate member having a longitudinal axis, a distal end to be inserted through the portal into the body, a proximal end and a cross-sectional configuration having a periphery;
- a housing mounting said proximal end of said cylindrical member to be disposed externally of the body;
- a lumen through said cylindrical member and said housing providing a passage for receiving surgical instruments to be introduced in the body; and
- a lip defined by a protrusion on said elongate member proximally spaced from said distal end, said protrusion tapering in a distal direction from said lip to said distal end and having a periphery spaced outwardly from said periphery of said elongate member to be disposed within the body, said elongate member periphery being disposed within said lip periphery, said lip including a surface substantially perpendicular to said longitudinal axis for engaging the wall of the body with said distal end inserted in the body to prevent backing out of said distal end from the body.

5. A cannula as recited in claim 4 wherein said lumen is substantially circular in cross-section and has a diameter for receiving various sizes of surgical instruments.

6. A cannula as recited in claim 5 further including a valve assembly mounted in said lumen within said housing and having means allowing passage therethrough of surgical instruments of various sizes.

7. A cannula as recited in claim 6 wherein said housing includes a forward section mounting said elongate member and a rearward section terminating at a rearward end and wherein said valve assembly is disposed in said rearward section.

8. A cannula as recited in claim 7 wherein said lumen includes a passage in said rearward section and a cavity in said forward section communicating with said passage and further including an annular ledge within said cavity for mounting said valve assembly.

9. A cannula as recited in claim 8 further including a cap mounted on said housing at said rearward end and having an aperture allowing passage therethrough of surgical instruments.

10. A cannula for introducing surgical instruments in the body through anatomical tissue of a wall of the body including
- a tubular member having a distal end to be inserted through the wall of the body, a proximal end and a circumference;
- a housing mounting said proximal end of said cylindrical member to be disposed externally of the body;
- a lumen in said tubular member and said housing for receiving surgical instruments to be introduced in the body; and
- a lip on said tubular member including a substantially flat surface spaced proximally of said distal end and having a periphery rigidly spaced outwardly of said circumference for being inserted through the wall of the body to engage the wall with said distal end disposed in the body to prevent backing out of said distal end from the wall.

11. A cannula as recited in claim 10 wherein said periphery is annular in configuration.

12. A cannula as recited in claim 11 wherein said circumference of said tubular member id disposed concentrically with said periphery of said surface.

13. A cannula as recited in claim 12 wherein the wall of the body includes an internal surface and said lip surface engages the internal surface.

14. A cannula as recited in claim 13 wherein the lip surface is spaced proximally from said distal end a minimal distance.

15. A cannula as recited in claim 14 further including a protrusion joining said lip surface to said tubular member, said protrusion tapering in a distal direction from said lip surface to said distal end.

16. A cannula for introducing surgical instruments in the body through anatomical tissue of a wall of the body having an internal surface including
- a tubular member having a distal end to be inserted through the wall of the body, a proximal end and a circumference;
- a housing mounting said proximal end of the cylindrical member to be disposed externally of the body;
- a lumen in said tubular member and said housing for receiving surgical instruments to be introduced in the body;
- an annular lip on said tubular member including a wall engaging surface spaced proximally of said distal end a minimal distance, said lip having a periphery, said circumference being disposed concentrically with said periphery, said periphery being spaced outwardly of said circumference for being inserted through the wall of the body to position said wall engaging surface in engagement with the internal surface of the wall with said distal end disposed in the body to prevent backing out of said distal end from the wall; and
- a tapered surface having a truncated conical configuration joining said lip to said tubular member, said tapered surface tapering in a distal direction from said lip to said distal end.

17. A method of introducing a surgical instrument at an operative site in the body in endoscopic procedures including the steps of
- forming a portal of minimal size in tissue of a wall of the body adjacent the operative site;
- visualizing the operative site endoscopically;
- inserting a lip on an end of a cannula into the body through the portal with a periphery of the lip rigidly disposed outwardly of a periphery of the cannula;
- positioning a substantially planar surface of the lip against an internal surface of the wall to prevent backing out of the cannula from the body; and
- introducing a surgical instrument at the operative site through a lumen of the cannula.

18. A method of introducing a surgical instrument as recited in claim 17 wherein said step of forming a portal includes forming the portal to be just large enough to receive the cannula.

19. A method of introducing a surgical instrument as recited in claim 18 wherein said step of inserting includes inserting the end of the cannula to protrude from the internal surface a minimal distance.

20. A method of introducing a surgical instrument as recited in claim 19 wherein said step of introducing includes introducing the surgical instrument through a valve assembly in the lumen of the cannula.

21. A method of introducing a surgical instrument as recited in claim 20 wherein said step of introducing includes, prior to introducing the surgical instrument through the valve assembly, the step of inserting the surgical instrument through a cap on the cannula.

22. A method of introducing a surgical instrument at the knee in arthroscopic procedures including the steps of
   forming a portal of minimal size in tissue adjacent the knee;
   visualizing the knee with an arthroscope;
   inserting an end of a cannula through the portal;
   positioning a lip on the end of the cannula against an internal surface of the tissue to prevent backing out of the cannula from the tissue; and
   introducing a surgical instrument at the knee through a lumen of the cannula.

23. A method of introducing a surgical instrument at the knee as recited in claim 22 wherein said step of forming a portal includes forming a posteromedial portal.

24. A method of introducing a surgical instrument at the knee as recited in claim 22 wherein said step of forming a portal includes forming a posterolateral portal.

25. A method of preventing extravasation when introducing a surgical instrument at an operative site in the body through a portal of minimal size in endoscopic procedures including the steps of
   forming a portal of minimal size through tissue forming a wall of the body adjacent the operative site;
   visualizing the operative site endoscopically;
   inserting an end of a cannula into the body through the portal;
   positioning an annular, substantially planar lip on the end of the cannula disposed within the body in engagement with an internal surface of the wall; and
   introducing a surgical instrument at the operative site through a lumen of the cannula.

* * * * *

UNITED STATES PATENT AND TRADEMARK OFFICE
CERTIFICATE OF CORRECTION

PATENT NO.   :  5,234,455

DATED        :  August 10, 1993

INVENTOR(S)  :  James S. Mulhollan

It is certified that error appears in the above-identified patent and that said Letters Patent is hereby corrected as shown below:

Column 2, line 21, delete "3,896,803" and insert --3,896,804--; and

Column 9, line 2, delete "the" and insert --said--.

Signed and Sealed this

Fifteenth Day of March, 1994

*Attest:*

BRUCE LEHMAN

*Attesting Officer*  *Commissioner of Patents and Trademarks*